United States Patent
Jäger et al.

(10) Patent No.: US 10,703,709 B2
(45) Date of Patent: Jul. 7, 2020

(54) METHOD FOR PRODUCING ANILINE OR AN ANILINE CONVERSION PRODUCT

(71) Applicant: Covestro Deutschland AG, Leverkusen (DE)

(72) Inventors: Gernot Jäger, Köln (DE); Thomas Hamedinger, Leverkusen (DE); Giulio Lolli, Köln (DE); Amgad Salah Moussa, London (GB); Guenter Olf, Zülpich (DE)

(73) Assignee: Covestro Deutschland AG, Leverkusen (DE)

( * ) Notice: Subject to any disclaimer, the term of this patent is extended or adjusted under 35 U.S.C. 154(b) by 25 days.

(21) Appl. No.: 16/311,205

(22) PCT Filed: Jun. 27, 2017

(86) PCT No.: PCT/EP2017/065913
§ 371 (c)(1),
(2) Date: Dec. 19, 2018

(87) PCT Pub. No.: WO2018/002088
PCT Pub. Date: Jan. 4, 2018

(65) Prior Publication Data
US 2019/0233365 A1    Aug. 1, 2019

(30) Foreign Application Priority Data
Jun. 29, 2016 (EP) ..................... 16177000

(51) Int. Cl.
*C07C 209/68* (2006.01)
*C07C 209/78* (2006.01)
*C12P 13/00* (2006.01)

(52) U.S. Cl.
CPC .......... *C07C 209/68* (2013.01); *C07C 209/78* (2013.01); *C12P 13/001* (2013.01)

(58) Field of Classification Search
None
See application file for complete search history.

(56) References Cited

U.S. PATENT DOCUMENTS

| | | |
|---|---|---|
| 4,233,459 A | 11/1980 | Kilpper et al. |
| 4,328,339 A | 5/1982 | Kilpper et al. |
| 4,851,570 A | 7/1989 | Zaby et al. |
| 5,053,539 A | 10/1991 | Yano et al. |
| 5,286,760 A | 2/1994 | Bolton et al. |
| 7,230,130 B2 | 6/2007 | Strofer et al. |
| 7,253,321 B2 | 8/2007 | Hagen et al. |

(Continued)

FOREIGN PATENT DOCUMENTS

WO    2015124686 A1    8/2015

OTHER PUBLICATIONS

Wiklund et al., Current Organic Synthesis, 2006, 3, 379-402.
(Continued)

*Primary Examiner* — Erin M. Bowers
(74) *Attorney, Agent, or Firm* — Donald R. Palladino

(57) ABSTRACT

The invention relates to a method for producing aniline or products that are obtained by further chemical reaction of aniline (aniline derivatives), involving decarboxylation of aminobenzoic acid, particularly ortho-aminobenzoic acid, in which one portion of the previously formed crude aniline is recirculated in the decarboxylation step. The aminobenzoic acid is obtained enzymatically or chemically, preferably enzymatically.

18 Claims, 1 Drawing Sheet

(56) References Cited

U.S. PATENT DOCUMENTS

| | | |
|---|---|---|
| 7,547,801 B2 | 6/2009 | Pohl et al. |
| 7,692,042 B2 | 4/2010 | Dugal et al. |
| 8,079,752 B2 | 12/2011 | Rausch et al. |
| 8,097,751 B2 | 1/2012 | Koch et al. |
| 8,455,691 B2 | 6/2013 | Sommer et al. |
| 2007/0238901 A1 | 10/2007 | Dugal et al. |
| 2010/0324336 A1 | 12/2010 | Sommer et al. |
| 2017/0066713 A1 | 3/2017 | Jaeger et al. |
| 2017/0152535 A1 | 6/2017 | Jaeger et al. |

OTHER PUBLICATIONS

Stevens et al., Canadian Journal of Chemistry, 1952, 30 (7), 529-540.
McMaster and Shriner, Journal of the American Chemical Society, 1923, 45 (3), 751-753.
Lorz et al., Phthalic Acid and Derivatives in Ullmann's Encyclopedia of Industrial Chemistry, 2007, vol. 27, pp. 140-141 Weinheim, Wiley-VCH.
Balderas-Hemandez, V. E. et al., "Metabolic engineering for improving anthranilate synthesis from glucose in *Escherichia coli*", Microbial Cell Factories, 2009, 8, 19 (doi: 10.118611475-2859-8-19).
Maki et al., Benzoic Acid and Derivatives in Ullmann's Encyclopedia of Industrial Chemistry, 2000, vol. 5, pp. 338 ff Weinheim, Wiley-VCH.
O. Kamm et al., p-Nitrobenzoic acid in Organic Syntheses, vol. 1, 1941, pp. 392 ff.
Kamm et al., Methyl m nitrobenzoate in Organic Syntheses, vol. 1, 1941, pp. 372 ff.
Kamm et al., m-Nitrobenzoic acid in Organic Syntheses, vol. 1, 1941, pp. 391 ff.

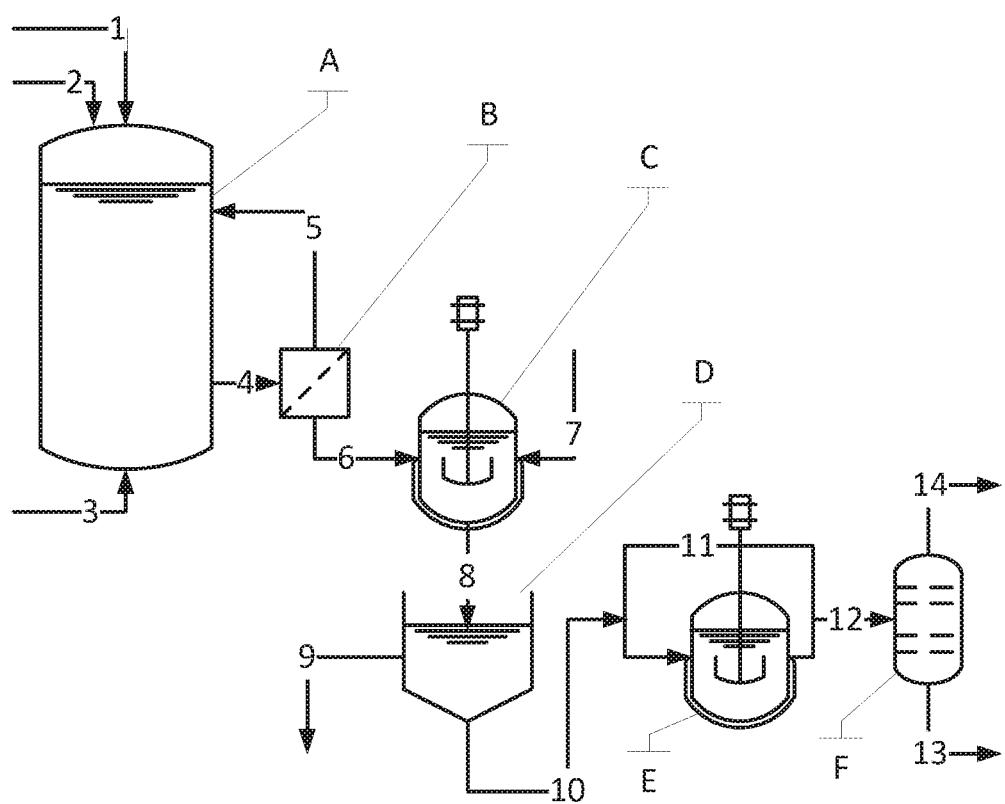

METHOD FOR PRODUCING ANILINE OR AN ANILINE CONVERSION PRODUCT

CROSS-REFERENCE TO RELATED APPLICATIONS

This application is a national stage application under 35 U.S.C. § 371 of PCT/EP2017/065913, filed Jun. 27, 2017, which claims the benefit of European Application No. 16177000.3, filed Jun. 29, 2016, both of which are being incorporated by reference herein.

FIELD

The present invention relates to a method for producing aniline or products obtained by further chemical reaction of aniline (referred to below as "aniline conversion products" or "aniline derivatives"; both terms are used synonymously in the context of the present invention), comprising decarboxylation of aminobenzoic acid, especially ortho-aminobenzoic acid, wherein a portion of the crude aniline previously formed is recirculated to the decarboxylation step. The aminobenzoic acid is obtained by fermentation or chemically, preferably by fermentation.

BACKGROUND

The production of aniline by decarboxylation of aminobenzoic acid is known in principle in the prior art; see for example Per Wiklund et al., *Current Organic Synthesis*, 2006, 3, 379-402. Stevens et al., *Canadian Journal of Chemistry*, 1952, 30 (7), 529-540, reports that an aqueous solution of ortho-aminobenzoic acid could be decarboxylated to aniline in the presence of 0.75N sulfuric acid at 100° C. in 6 hours with a yield of 56%. It had previously been reported in MacMaster and Shriner, *J. Am. Chem. Soc.*, 1923, 45 (3), 751-753 that under similar conditions (in boiling water) but in the absence of acid, ortho-aminobenzoic acid was decarboxylated to aniline in 7 hours with a yield of only 27%.

Publications are also found for this purpose in the recent patent literature; see for example WO 2015/124686 A1 and WO 2015/124687 A1. WO 2015/124686 A1 describes the thermal decarboxylation of ortho-aminobenzoic acid in an aqueous medium in the presence of or without catalyst. WO 2015/124687 A1 describes the catalytic decarboxylation by zeolite catalysis in 1-decanol as solvent. Both applications furthermore describe the further conversion of the aniline thus produced to aniline derivatives such as di- and polyamines of the diphenylmethane series and the corresponding isocyanates.

The aminobenzoic acid starting compound can be obtained chemically or preferably by fermentation.

The chemical production of aminobenzoic acid is described in the literature. A suitable synthesis route (with yields >98%) is, for example, the reaction of phthalimide with sodium hypochlorite. Phthalimide can be obtained in turn from phthalic anhydride and ammonia. The whole process is well-known and is described, for example, in Lorz et al., *Phthalic Acid and Derivatives* in Ullmann's Encyclopedia of Industrial Chemistry, Volume 27, pp. 140-141, Weinheim, Wiley-VCH. An industrial process is also described in the patent literature; see e.g. DE 29 02 978 A1 and EP 0 004 635 A2.

The production by fermentation of aminobenzoic acid is described in the literature. For the production of aminobenzoic acid by fermentation, reference is made by way of example to Balderas-Hemandez, V. E. et al., "Metabolic engineering for improving anthranilate synthesis from glucose in *Escherichia coli*", *Microb. Cell. Fact.* 2009, 8, 19 (doi: 10.118611475-2859-8-19). Publications can also be found in the patent literature for this purpose; see for example the already mentioned applications WO 2015/124686 A1 and WO 2015/124687 A1 and the literature cited therein in each case.

Fermentation processes generally proceed in an aqueous medium and in the case of production of aminobenzoic acid generally afford aqueous solutions (fermentation broths) with a content by mass of aminobenzoic acid in the range from 10.0 g/L to 100 g/L. The approach described in WO 2015/124686 A1, the direct decarboxylation of the aqueous solution of ortho-aminobenzoic acid, optionally after removal of biomass, is certainly not unattractive per se. However, the method described in WO 2015/124686 A1 requires the extraction of aniline formed in the decarboxylation with an organic solvent extraneous to the system (an alcohol, phenol, amide, ether or aromatic hydrocarbon; in particular, 1-dodecanol is emphasized as a suitable solvent), which is associated unavoidably with additional costs and additional purification complexity (separation of aniline from 1-dodecanol).

WO 2015/124687 A1 describes the procedure of decarboxylation inter alia in water or in an organic solvent extraneous to the system, in particular 1-dodecanol, optionally in the mixture with aniline (cf. page 18, lines 28 and 29). The disadvantages outlined previously of the use of an organic solvent extraneous to the system are therefore also relevant to these embodiments of the decarboxylation. In addition, this document also describes the possibility of carrying out the decarboxylation in aniline (without 1-dodecanol; see FIGS. 35 and 37 to 38 and the accompanying text passages), optionally in the presence of 10% by mass water (see FIG. 36 and the accompanying text passages). Although the document makes no explicit reference to the origin of the aniline used, it is obvious to those skilled in the art from the context that it is pure aniline. The description of this method variant however does not go beyond the illustration of the fundamental possibility of such a decarboxylation of aminobenzoic acid from different sources of aniline. Process engineering details for the source and configuration of the feeding of the aniline to be used in the decarboxylation step in a preferably continuously operating industrial scale process are not to be found in the document.

Further improvements in the production of aniline and aniline conversion products by decarboxylation of aminobenzoic acid, particularly obtained by fermentation, therefore would be desirable. In particular, it would be desirable to be able to design the simplest possible method and without using solvent extraneous to the system (such as 1-dodecanol), in order to increase the economic viability of the method and thus to make its use in industrial scale production more attractive. Furthermore, it would be desirable to design improvements to the decarboxylation step so that the purification of the aniline obtained, preferably carried out by distillation, following the decarboxylation, is not difficult or is even simplified.

SUMMARY

Taking account of the above, the present invention provides a method for producing aniline or an aniline conversion product, comprising the following steps:

(I) decarboxylating aminobenzoic acid, particularly ortho-aminobenzoic acid, to aniline in a reactor in the presence of a catalyst, wherein a stream containing aniline (also called "crude aniline" hereinafter) is withdrawn from the reactor;

(II) purifying a portion of the stream containing aniline withdrawn in step (I) to obtain aniline, preferably by distillation;

(III) recirculating another portion of the stream containing aniline withdrawn in step (I) (also called "recycled aniline" hereinafter) into the reactor of step (I);

(IV) optionally further reacting the aniline purified in step (II) to give an aniline conversion product.

BRIEF DESCRIPTION OF THE DRAWING

Various features and characteristics of the invention described in this specification may be better understood by reference to the accompanying FIG. 1 which is shows a preferred configuration of the method according to the invention.

DETAILED DESCRIPTION

Completely surprisingly, it has been found that recirculation of a portion of the stream containing aniline withdrawn in step (I) can be carried out successfully in the reactor of step (I), despite the recirculation also of by-products inevitably associated thereto that are potentially harmful to the catalyst, and thus the addition of organic solvent extraneous to the system is superfluous. (In the context of the present invention, "organic solvents extraneous to the system" are understood to mean those organic solvents which are not inherent to the method, i.e., are not in any case necessarily present in the method Aniline, which is present in the stream recirculated to the reactor of step (I) in the context of step (III), can be interpreted in this sense as a solvent inherent to the method. In the context of this invention, furthermore, the aniline fed additionally to the reactor of step (I) in preferred embodiments optionally from an external source is also understood to mean a solvent inherent to the method, since aniline is the product of the method). It has specifically been found that, surprisingly, by recirculating a portion of the crude aniline, a solvent is available providing fully sufficient and satisfactory results for the successful performance of the reaction.

In the context of the present invention, the term "aniline conversion product" refers to a product which is obtained by further chemical conversion of aniline.

There follows firstly a brief summary of various possible embodiments of the invention:

In a first embodiment of the invention, which may be combined with all other embodiments, in addition to the stream containing aniline recirculated in step (III) to the reactor of step (I), a further aniline stream is fed of purified, preferably distilled aniline, especially aniline having an aniline content determined by gas chromatography of at least 99.00% by mass, preferably at least 99.50% by mass, especially preferably at least 99.90% by mass, based on the total mass of the aniline stream additionally fed, wherein the aniline additionally fed to the reactor of step (I) in this manner accounts for at most 60%, preferably 1.0% to 50%, preferably 5.0% to 20%, of the total aniline fed to the reactor of step (I).

In a second embodiment of the invention, which is a particular configuration of the first embodiment, the concentration of aniline in the stream containing aniline which is removed from the reactor of step (I) is monitored and, when a shortfall in the concentration of aniline of a previously set value is detected, the proportion of aniline of the aniline stream additionally fed to the reactor that is composed of purified, preferably distilled aniline, especially aniline having an aniline content determined by gas chromatography of at least 99.00% by mass, preferably at least 99.50% by mass, especially preferably at least 99.90% by mass, based on the total mass of the aniline stream additionally fed, is increased to a value of at most 60% of the aniline fed in total to the reactor of step (I).

In a third embodiment of the invention, which may be combined with all other embodiments, the stream containing aniline withdrawn from the reactor of step (I) is divided into two streams in a ratio by mass in the range from 9.0:1 to 1:9.0, preferably in the range from 1.5:1 to 1:1.5, of which one, preferably the larger, is fed to the recirculation of step (III) and the other to the purification of step (II).

In a fourth embodiment of the invention, which may be combined with all other embodiments, step (I) is conducted at a temperature in the range from 140° C. to 240° C. and at an absolute pressure in the range from 1.00 bar to 20.0 bar, preferably at a temperature in the range from 160° C. to 220° C. and at an absolute pressure in the range from 1.00 bar to 15.0 bar, particularly preferably at a temperature in the range from 180° C. to 200° C. and at an absolute pressure in the range from 4.00 bar to 10.0 bar.

In a fifth embodiment of the invention, which may be combined with all other embodiments, the reactor of step (I) is a slurry phase reactor, wherein the catalyst is used at a concentration in the range from 0.100% by mass to 50.0% by mass, preferably in the range from 10.0% by mass to 30.0% by mass, based on the total mass of the liquid reaction mixture, or a stirred tank reactor, or a tubular reactor with a catalyst bed, wherein the catalyst is present particularly as particles and preferably is fixed in the catalyst bed.

In a sixth embodiment of the invention, which may be combined with all other embodiments, the catalyst used in step (I) is a zeolite catalyst, preferably a zeolite of type Y in protonated form.

In a seventh embodiment of the invention, which may be combined with all other embodiments, the aminobenzoic acid to be decarboxylated in step (I) is provided by the following step (I-0) to be carried out prior to step (I):

(I-0) fermentation of a raw material, which comprises at least one fermentable carbon-containing compound preferably selected from the group consisting of starch hydrolysate, sugar cane juice, sugar beet juice and hydrolysates of lignocellulose-containing raw materials, and a nitrogen-containing compound, preferably selected from the group consisting of ammonia gas, ammonia water, ammonium salts (especially ammonium sulfate and ammonium chloride) and urea, in a fermentation reactor using microorganisms to obtain a fermentation broth; which is then optionally followed by the following work-up steps:

(α) removing the microorganism from the fermentation broth and/or (β) decolorizing the fermentation broth or, in the case of step (α) being carried out, the fermentation broth depleted of microorganisms obtained in step (α).

In an eighth embodiment of the invention, which is a particular configuration of the seventh embodiment, the following step is carried out after step (I-0) and prior to step (I):

(I-0) (a) enrichment of the aminobenzoic acid by one of the following measures:
  (1) evaporation of the fermentation broth, or
  (2) precipitation by acid treatment combined with at least partial removal of the aminobenzoic acid that separates out from the acid-treated fermentation broth.

In a ninth embodiment of the invention, which is a particular configuration of the eighth embodiment, step (I-0) (a) is carried out according to variant (2) and comprises the following:

(i) treatment, preferably single-stage treatment, of the fermentation broth obtained in step (I-0), optionally after carrying out step (α) and/or step (β), in a reactor with acid such that aminobenzoic acid separates out from the fermentation broth, wherein preferably the pH of the resulting mixture is adjusted to a value in the range from 3.0 to 4.7, preferably in the range from 3.2 to 3.7, particularly preferably in the range from 3.4 to 3.6;
(ii) at least partially removing the aminobenzoic acid that separates out in step (I-0) (a) (i) from the acid-treated fermentation broth;
(iii) optional further purification of the aminobenzoic acid obtained in step (I-0) (a) (ii), preferably by washing with water.

In a tenth embodiment of the invention, which is a particular embodiment of the ninth embodiment, the acid used in step (I-0) (a) (i) comprises hydrochloric acid, sulfuric acid and/or phosphoric acid, wherein the acid used in step (I-0) (a) (i) preferably comprises hydrochloric acid at a concentration of 15% by mass to 37% by mass, and particularly preferably does not comprise any further acid in addition to this hydrochloric acid with the exception of optionally added recycled acid-treated fermentation broth from step (I-0) (a) (ii).

In an eleventh embodiment of the invention, which is a particular configuration of the seventh, eighth, ninth or tenth embodiment, the microorganisms used in step (I-0) comprise a species selected from the group consisting of *Escherichia coli, Pseudomonas putida, Corynebacterium glutamicum, Ashbya gossypii, Pichia pastoris, Hansenula polymorpha, Yarrowia lipolytica, Zygosaccharomyces bailii* and *Saccharomyces cerevisiae*, and consist preferably only of representatives precisely of one of these species, wherein very particular preference is given to *Corynebacterium glutamicum* ATTC 13032.

In a twelfth embodiment of the invention, which may be combined with all other embodiments, especially with the seventh, eighth, ninth, tenth or eleventh embodiment, to the stream containing aniline fed back in step (III) to the reactor of step (I) is added solid or dissolved or suspended aminobenzoic acid, preferably specifically in such an amount that the mass stream of this solid or dissolved or suspended aminobenzoic acid supplied corresponds to the mass stream of the portion of the stream containing aniline withdrawn in step (I) fed to the purification in step (II).

In a thirteenth embodiment of the invention, which is a particular configuration of the twelfth embodiment combined with the eighth, ninth, tenth or eleventh embodiment, to the stream containing aniline recirculated in step (III) to the reactor of step (I) is added solid or dissolved or suspended aminobenzoic acid, wherein this originates from step (I-0) (a), especially from step (I-0) (a) (ii) or from step (I-0) (a) (iii), and contains water, and wherein preferably the water content and the amount of this solid or dissolved or suspended aminobenzoic acid are adjusted so that the water content of the liquid reaction mixture in step (I) is in the range from 0.10% by mass to 40% by mass, preferably 0.15% by mass to 20% by mass, based on the total mass of the liquid reaction mixture of step (I).

In a fourteenth embodiment of the invention, which may be combined with each one of the first to eleventh embodiments, and particularly with the seventh, eighth, ninth, tenth or eleventh embodiment, the stream containing aniline recirculated in step (III) and the aminobenzoic acid to be decarboxylated are fed to the reactor of step (I) via separate feed units.

The embodiments briefly outlined previously and further configurations of the invention are described in greater detail below. Various embodiments can be freely combined here with one another, unless the opposite is apparent to the person skilled in the art from the overall context.

Aminobenzoic acid occurs in three isomeric forms (ortho-, meta- and para-aminobenzoic acid). In principle, the method according to the invention can be applied to all three isomers, either in isomerically pure form or as mixtures of different isomers. It applies to all embodiments of the present invention that the aminobenzoic acid to be decarboxylated in step (I) preferably comprises the ortho-isomer. The aminobenzoic acid to be decarboxylated in step (I) particularly preferably comprises at least 50.0 mol %, especially preferably at least 90.0 mol % of the ortho-isomer, based on the total amount of all isomers of aminobenzoic acid present. The aminobenzoic acid to be decarboxylated in step (I) very exceptionally preferably consists of the ortho-isomer in isomerically pure form (i.e. isomeric purity >99.0 mol %).

The reactors suitable for carrying out step (I) are in principle the customary reactor types familiar to those skilled in the art in process technology such as stirred tank reactors (preferably with fixed bed catalyst), continuous stirred tank reactors, especially continuous stirred tank reactors (CSTR) with fixed bed catalyst, plug flow reactors with fixed bed catalyst or slurry phase reactors (also called suspension reactors) with catalyst recirculation or catalyst recovery.

The expression "in a reactor" includes in accordance with the invention also embodiments in which two or more reactors of a reactor cascade are connected in series, i.e. the liquid product discharge of one reactor flows into the next reactor for further completion of the conversion. It is only possible to feed the reactants (i.e. the aminobenzoic acid to be decarboxylated and recirculated crude aniline) to the first reactor of a reactor cascade. However, it is also possible to feed the aminobenzoic acid to be decarboxylated and recirculated crude aniline to each reactor of a reactor cascade. The stream containing aniline, which is fed to steps (II) and (III), is withdrawn from the final reactor of the reactor cascade.

Catalysts suitable for carrying out step (I) are catalysts familiar to those skilled in the art such as aqueous acids such as sulfuric acid, nitric acid and hydrochloric acid; solid acids such as zeolites and Si—Ti molecular sieves, solid bases such as hydroxyapatite and hydrotalcite; polymeric acids such as ion exchange resins (particularly Amberlyst). If the catalyst is used in the form of particles or in powder form, a preferred embodiment of the invention consists of slurrying the catalyst in the liquid reaction mixture, preferably by stirring. For this purpose, a slurry phase reactor (also called suspension reactor) is particularly suitable, wherein the catalyst is used at a concentration in the range from 0.100% by mass to 50.0% by mass, preferably in the range from 10.0% by mass to 30.0% by mass, based on the total mass of the liquid reaction mixture. In another preferred embodiment, the catalyst is arranged in a catalyst bed in a tubular reactor, wherein in this embodiment the catalyst present particularly in particles (e.g. spheres) is preferably fixed in the catalyst bed, for example arranged between sieve plates. Irrespective of the type of reactor used, the catalyst used in step (I) is preferably a zeolite catalyst, particularly preferably a zeolite of type Y in protonated form (H form). The arrangement of the catalyst, particularly present in particle form, in a fixed bed is of course not restricted to tubular reactors but can in principle also be applied to stirred reactors. Furthermore, it is possible to use the catalyst in monolithic form.

In the decarboxylation of step (I), the following reaction parameters may be maintained for example:

Temperature preferably in the range from 140° C. to 240° C. and absolute pressure preferably in the range from 1.00 bar to 20.0 bar, Temperature particularly preferably in the range from 160° C. to 220° C. and absolute pressure particularly preferably in the range from 1.00 bar to 15.0 bar, Temperature especially preferably in the range from 180° C. to 200° C. and absolute pressure especially preferably in the range from 4.00 bar to 10.0 bar, The stream containing aniline, prior to its withdrawal from the reactor, preferably passes through a filter in order to prevent solid particles (e.g. catalyst particles) being entrained.

Step (I) is preferably carried out continuously, i.e. the reactants (i.e. aminobenzoic acid and recirculated aniline fed in step (III)) are fed continuously to the reactor and the product (i.e. crude aniline) is withdrawn continuously from the reactor. In one variant of this procedure, at least portions of the catalyst are also exchanged permanently or at intervals in the continuous operation in order to prevent depletion of its performance capability. A discontinuous process regime (so-called batchwise mode) is also possible however. In one variant of the discontinuous procedure (so-called "Fed batch mode"), the reactants are fed continuously to the reactor as long as the reactor volume allows it without products being removed from the reactor. The reaction is interrupted after addition of the maximum possible amount of reactants and the product mixture is withdrawn from the reactor.

In an alternative preferred embodiment, a process regime is also feasible in which the reactants (i.e. aminobenzoic acid and recirculated aniline fed in step (III)) are fed continuously to the reactor and the product (i.e. crude aniline) is withdrawn continuously from the reactor, but consumed catalyst is not removed in the continuous operation, rather fresh catalyst is added (either permanently or at intervals) instead up until the time at which the maximum amount of catalyst specified by the reactor volumes present has been reached in the reactor, and then the reactor is taken out of operation for the purposes of cleaning and catalyst exchange.

In all embodiments, it is preferable to carry out step (I) with exclusion of oxygen. To inertize the reactor, inert gases such as nitrogen, carbon dioxide or noble gases are suitable.

In accordance with the invention, the use of organic solvents extraneous to the system in step (I) of the present invention is superfluous. Therefore, in a preferred configuration of the invention, step (I) is carried out in the absence of organic solvent extraneous to the system. This applies to all embodiments of step (I) described and the remaining steps of the method according to the invention.

The stream containing aniline withdrawn from the reactor of step (I) is divided in accordance with the invention. A portion of this stream is purified in step (II) to obtain aniline. This purification can be effected by methods familiar to those skilled in the art. In particular, the purification includes at least one distillation step, upstream of which a water removal by phase separation can be effected. The purification may also include a base treatment for removing acidic impurities before, during or after the distillation step. Suitable configurations are described, for example, in EP-A-1 845 079, EP-A-1 845 080, EP-A-2 263 997 and EP-A-2 028 176. (These documents are concerned with the purification of aniline which has been obtained by hydrogenation of nitrobenzene; the purification steps of the crude aniline described are also applicable however to aniline produced in other ways.)

In accordance with the invention, a further portion of the stream containing aniline withdrawn from the reactor of step (I) (the product stream of step (I), so-called "crude aniline") is recirculated to the reactor of step (I) (step (III) of the method according to the invention). In one embodiment of the invention, aniline is fed to the reactor of step (I) only by means of this recirculation of the stream containing aniline in step (III).

Irrespective of this, it is preferable to recirculate the product stream withdrawn from the reactor directly without further work-up steps to the reactor of step (I) after removing the portion intended for step (II). In a preferred configuration of the invention, the stream containing aniline withdrawn from the reactor of step (I) is divided into two streams in a ratio by mass in the range from 9.0:1 to 1:9.0, preferably in the range from 1.5:1 to 1:1.5, of which one, preferably the larger, is fed to the recirculation of step (III) and the other to the purification of step (II).

In a further preferred configuration of the invention, a further aniline stream from an external source (for example from the aniline stream obtained after passing through the purification of step (II)) can be fed to the reactor of step (I) in addition to the stream containing aniline recirculated in step (III). Purified (preferably distilled) aniline is suitable as additionally fed aniline stream, specifically especially aniline having an aniline content determined by gas chromatography of at least 99.00% by mass, preferably at least 99.50% by mass, particularly preferably at least 99.90% by mass, based on the total mass of the aniline stream additionally fed. The aniline additionally fed to the reactor of step (I) in this manner accounts for not more than 60%, preferably from 1.0% to 50%, particularly preferably from 5.0% to 20%, of the total aniline fed to the reactor of step (I). (The expression total aniline fed refers here and hereinafter to aniline as such. Therefore, if by way of example a stream 1 containing aniline (recirculated aniline) is fed to the reactor in step (III) at x kg/h, in which the proportion by mass of aniline in this stream is $w_1$, and an aniline stream 2 (purified aniline additionally fed) having a proportion by mass of aniline $w_2$ is further fed to the reactor at y kg/h, the total mass of aniline fed to the reactor per hour is $x \cdot w_1 + y \cdot w_2$. The proportion by mass of aniline in the recirculated aniline can easily be determined by those skilled in the art, particularly by high performance liquid chromatography (HPLC) or gas chromatography, wherein in the (unlikely) case of significant deviations between individual determination methods HPLC is definitive. Should the product stream determined for recirculation in step (III) contain impurities detrimental to the decarboxylation to a problematic extent (detectable by a decrease of the aniline concentration, possibly linked to an increase of the concentration of by-products), it is preferable to increase the proportion of purified (preferably distilled) aniline additionally fed (especially aniline which has at least partially passed through the purification of step (II)—for example only the first stage of a multi-stage distillation), of which in terms of the total aniline fed to the reactor of step (I), it forms a proportion of at most 60% of the total aniline fed to the reactor of step (I). It is therefore not required to further process the product stream withdrawn from the reactor prior to recirculation, since potentially interfering impurities can be diluted in this manner into a harmless concentration range. This measure is implemented if the concentration of aniline in the stream containing aniline withdrawn from the reactor of step (I) falls below a previously set concentration. The aniline concentration, based on the total mass of the stream containing aniline, which is withdrawn from the reactor of step (I), can be determined preferably by HPLC or gas chromatography, wherein in case of doubt the value determined by gas chromatography is definitive. The aniline concentration can be monitored online or by sampling at discrete intervals (particularly at least once every 24 hours). The value to be determined for this aniline concentration that preferably it should not fall below in the stream containing aniline withdrawn from the reactor of step (I) is dependent on the precise conditions in step (I) (which for example significantly affect the water content of the stream containing aniline) and the constraints prevailing at a production site, particularly the capability of the devices (e.g. distillation columns) available for the purification in step (II). A generic value cannot therefore be specified, but can be readily determined by those skilled in the art by simple preliminary experiments and/or simulations.

The aminobenzoic acid to be decarboxylated in step (I) can be obtained in principle in any way known to those skilled in the art. One possibility is the production of aminobenzoic acid by chemical routes. Preference is given to those methods that selectively afford the ortho-isomer of aminobenzoic acid. A suitable chemical method that may be mentioned by way of example is the reaction of phthalimide with sodium hypochlorite. Phthalimide can be obtained in turn from phthalic anhydride and ammonia. The whole process is well-known and is described, for example, in Lorz et al., *Phthalic Acid and Derivatives* in Ullmann's Encyclopedia of Industrial Chemistry, Volume 27, pp. 140-141, Weinheim, Wiley-VCH. An industrial process is also described in the patent literature; see e.g. DE 29 02 978 A1 and EP 0 004 635 A2.

Para-aminobenzoic acid can be prepared by chemical routes via the nitration of toluene with nitric acid, subsequent oxidation of the resulting para-nitrotoluene with oxygen to give para-nitrobenzoic acid and finally reduction with hydrazine to give para-aminobenzoic acid. The entire process is described, for example, in Maki et al., *Benzoic Acid and Derivatives* in Ullmann's Encyclopedia of Industrial Chemistry, Volume 5, pp. 338 ff., Weinheim, Wiley-VCH and in O. Kamm et al., *p-Nitrobenzoic acid* in Organic Syntheses, Volume 1, 1941, pp. 392 ff.

The preparation of meta-aminobenzoic acid is accomplished, for example, starting from methyl benzoate. Methyl meta-nitrobenzoate is obtained by nitrating methyl benzoate with nitric acid. This methyl ester is subsequently saponified with aqueous sodium hydroxide solution. Meta-nitrobenzoic acid is obtained after neutralization with hydrochloric acid, which is finally reduced with hydrazine to afford meta-aminobenzoic acid. The method is described, for example, in Maki et al., *Benzoic Acid and Derivatives* in Ullmann's Encyclopedia of Industrial Chemistry, Volume 5, pp. 338 ff., Weinheim, Wiley-VCH, in Kamm et al., *Methyl m-nitrobenzoate* in Organic Syntheses, Volume 1, 1941, pp. 372 ff. and in Kamm et al., *m-Nitrobenzoic acid* in Organic Syntheses, Volume 1, 1941, pp. 391 ff.

However, the aminobenzoic acid to be decarboxylated in step (I) is produced preferably by fermentation. Therefore, in a preferred configuration of the invention, the following step (I-0) is carried out prior to step (I), by means of which the aminobenzoic acid to be decarboxylated in step (I) is provided:

(I-0) fermentation of a raw material, which comprises at least
one fermentable carbon-containing compound preferably selected from the group consisting of starch hydrolysate, sugar cane juice, sugar beet juice and hydrolysates of lignocellulose-containing raw materials, and
a nitrogen-containing compound, preferably selected from the group consisting of ammonia gas, ammonia water, ammonium salts (especially ammonium sulfate and ammonium chloride) and urea,
in a fermentation reactor using microorganisms to obtain a fermentation broth.

Step (I-0) of the method according to the invention can be carried out by any procedure known from the prior art.

Depending on the pH at which the fermentation is carried out, aminobenzoic acid is obtained in step (I-0) not in the electroneutral form, but as aminobenzoate for example (for the type of isomer formed, this is unimportant, however). In the context of this invention in connection with step (I-0), for reasons of linguistic simplicity, aminobenzoic acid is regularly referred to, which is to be understood as including the cationic [i.e. diprotonated], anionic [i.e. deprotonated] and neutral [i.e. electroneutral] form of aminobenzoic acid. However, when it is evident from the constraints of a specifically outlined embodiment that the deprotonated form is formed for example, then this refers to aminobenzoate.

Preferred microorganisms for carrying out step (I-0) are bacteria or fungi, but in particular yeasts. Particular preference is given here to microorganisms of a species selected from the group consisting of *Escherichia coli, Pseudomonas putida, Corynebacterium glutamicum, Ashbya gossypii, Pichia pastoris, Hansenula polymorpha, Yarrowia lipolytica, Zygosaccharomyces bailii* and *Saccharomyces cerevisiae*. The microorganisms used in step (I-0) especially preferably consist only of representatives precisely of one of these species, wherein exceptionally special preference is given to *Corynebacterium glutamicum* ATTC 13032. The pH to be maintained in the fermentation is based on the microorganism used. Microorganisms such as *Corynebacterium glutamicum, Pseudomonas putida* or *Escherichia coli* are preferably cultured at neutral pH (i.e. at a pH in the range from 6.0 to 8.0). Microorganisms such as *Saccharomyces cerevisiae* in contrast are preferably cultured in acidic medium (i.e. at a pH in the range from 4.0 to 5.0).

In each case, the microorganism of step (I-0) is preferably selected such that the ortho-isomer of aminobenzoic acid is formed in the fermentation.

In a preferred configuration of the invention, bacteria are used as microorganisms. Reference is made here in particular to patent applications WO 2015/124686 A1 and WO 2015/124687 A1, in which a fermentation is described using bacteria that can be used in accordance with the invention (see for example WO 2015/124687 A1, (i) page 15, line 8 to page 16, line 30, (ii) example 1 (page 29, lines 4 to 26), (iii) example 3 (especially page 34, lines 10 to 18), (iv) example 4 (especially page 55, lines 9 to 3)). In particular, bacteria are used which are capable of converting a fermentable carbon-containing compound to aminobenzoic acid in the presence of a suitable nitrogen source, without the aminobenzoic acid thus formed being consumed again in internal cell biochemical processes such that aminobenzoic acid is enriched in the cell and finally migrates into the fermentation broth.

In another preferred configuration of the invention, yeasts are used as microorganisms. Reference is made here in particular to the still unpublished European patent application with the application number 16157777.0. In particular, yeast cells are used which are capable of converting a fermentable carbon-containing compound to aminobenzoic acid in the presence of a suitable nitrogen source, without the aminobenzoic acid thus formed being consumed again in internal cell biochemical processes such that aminobenzoic acid is enriched in the cell and finally migrates into the fermentation broth.

In order to obtain a bacterium of this kind or a yeast of this kind, two routes are available in principle which may also be combined in a preferred configuration:
 (i) The enzymatic reactions in the aminobenzoic acid metabolic pathway of the bacterial cell or yeast cell can be increased such that aminobenzoic acid is produced more rapidly than it is consumed.
 (ii) Subsequent reactions by which aminobenzoic acid is converted into further metabolites or products (e.g. tryptophan) can be reduced or switched off so that even the rate of aminobenzoic acid formation is sufficient in wild type strains to lead to enrichment of aminobenzoic acid in the cell.

Methods for obtaining bacteria or yeast cells with the properties specified above are known from the prior art. Suitable bacteria or yeast cells can be identified, for example, by screening for mutants which secrete aminobenzoic acid into the surrounding medium. The target-directed modification of key enzymes by genetic engineering is preferred however. Using customary genetic engineering methods, gene expression and enzyme activity can be enhanced, reduced or even completely suppressed at will. Recombinant strains are the result.

The bacteria or yeast cells which are capable of converting a fermentable carbon-containing compound to aminobenzoic acid in the presence of a nitrogen-containing compound particularly preferably comprise a modification to the anthranilate phosphoribosyltransferase activity, which reduces said enzyme activity. Due to this modification, the conversion of ortho-aminobenzoate to N-(5-phospho-D-ribosyl)anthranilate is reduced or completely suppressed. This causes an enrichment of aminobenzoic acid in the cell. The designation "anthranilate phosphoribosyltransferase activity" refers here to an enzyme activity by which the conversion of ortho-aminobenzoate to N-(5-phospho-D-ribosyl) anthranilate is catalyzed.

In yeasts, anthranilate phosphoribosyltransferase activity is genetically encoded by the native gene TRP4 (YDR354W). In the bacterium *Corynebacterium glutamicum*, anthranilate phosphoribosyltransferase activity is encoded by the trpD gene (cg3361, Cg13032, NCg12929). In the case of *Pseudomonas putida* the encoding is effected via the trpD gene (PP_042) within the trpDC operon.

The decrease described of the anthranilate phosphoribosyltransferase activity can be achieved in principle by three ways:
 (i) The regulation of the expression of the gene for anthranilate phosphoribosyltransferase activity can be modified such that the transcription of the gene or subsequent translation is reduced or suppressed.
 (ii) The nucleic acid sequence of the gene for anthranilate phosphoribosyl transferase activity can be modified such that the enzyme which is encoded by the modified gene has a lower specific activity.
 (iii) The native gene for anthranilate phosphoribosyl transferase activity can be replaced by another gene, which originates from a different organism, and can be coded for an enzyme having a specific anthranilate phosphoribosyl transferase activity which is lower than that of the native gene mentioned above (e.g. TRP4, trpD or trpDC).

Irrespective of which microorganism is used, the fermentation broth at the start of the fermentation in step (I-0) comprises recombinant cells of the microorganism used and at least one fermentable carbon-containing compound (and at least one nitrogen-containing compound as nitrogen source). The fermentation broth preferably also comprises further constituents selected from the group consisting of buffer systems, inorganic nutrients, amino acids, vitamins and further organic compounds which are required for the growth or housekeeping metabolism of the recombinant cells. The fermentation broth is water-based. After employing the fermentation process, the fermentation broth also comprises aminobenzoic acid, the desired fermentation product.

In the context of the present invention, a fermentable carbon-containing compound is understood to mean any organic compound or mixture of organic compounds which can be used by the recombinant cells of the microorganism used to produce aminobenzoic acid. The production of aminobenzoic acid can take place in this case in the presence or in the absence of oxygen.

Preference is given in this connection to those fermentable carbon-containing compounds which can additionally serve as energy and carbon source for the growth of the recombinant cells of the microorganism used. Particularly suitable are starch hydrolyzate, sugarcane juice, sugar beet juice and hydrolyzates from lignocellulose-containing raw materials. Likewise suitable are glycerol and C1 compounds, especially carbon monoxide.

If necessary, between the fermentation in step (I-0) and the decarboxylation in step (I), it is ensured by adjusting the pH that aminobenzoic acid is in the electroneutral form for carrying out the decarboxylation. In numerous cases, the fermentation broth after step (I-0) is basic to neutral or possibly slightly acidic (pH>4.0). In order to ensure that the aminobenzoic acid is in the electroneutral form for carrying out the decarboxylation, the fermentation broth obtained in step (I-0), optionally after carrying out step ($\alpha$) and/or step ($\beta$)—if this fermentation broth is not already sufficiently acidic—, is adjusted by treatment with an acid, preferably comprising hydrochloric acid, sulfuric acid and/or phosphoric acid, to a pH of the resulting mixture in the range from 3.0 to 4.7, preferably in the range from 3.2 to 3.7, particularly preferably in the range from 3.4 to 3.6. In the further embodiment outlined below with enrichment of aminobenzoic acid by precipitation (crystallization), this pH adjustment corresponds to step (I-0) (a) (i). Should the fermentation broth after step (I-0) be strongly acidic (pH<3.0), a pH in the aforementioned ranges is ensured by adding base (preferably aqueous sodium hydroxide solution, lime). If the pH of the fermentation broth after step (I-0), optionally after carrying out step ($\alpha$) and/or step ($\beta$), is in the range of 3.0 to 4.0, such as can be the case when using yeasts as microorganisms, in a preferred embodiment neither acid nor base is added but rather the fermentation broth is further processed directly without further pH adjustment. In this case, it is to be expected that crystals of aminobenzoic acid spontaneously precipitate and can be directly separated off.

Step (I-0) preferably comprises a work-up of the resulting fermentation broth. This work-up, which preferably follows on directly from the actual fermentation (which therefore takes places prior to the acid treatment [or base treatment] carried out, if necessary, outlined in the last paragraph), preferably comprises the following steps:
(α) removing the microorganism from the fermentation broth
and/or
(β) decolorizing the fermentation broth or, in the case of step (α) being carried out, the fermentation broth depleted of microorganisms obtained in step (α).

The removal of the microorganism from the fermentation broth in step (α) is known per se from the prior art and is effected in the context of the present invention particularly by filtration, settling, separation in hydrocyclones or centrifugation. A possible configuration of this step is described in WO 2015/124686 A1 and WO 2015/124687 A1. Reference is made here in particular to WO 2015/124687 A1, page 15, line 8 to page 15, line 17.

Irrespective of whether the microorganism is removed or not, step (I-0) may comprise if necessary a step (β) for decolorizing the fermentation broth or the fermentation broth depleted of microorganisms. This step (β) is preferably carried out such that fermentation broth or fermentation broth depleted of microorganisms is passed through a column with solid packing in order to remove colorants by means of adsorption. The possible solid phase used can be, for example, kieselguhr or ion exchange packings. Step (β) is then preferably carried out if such colored substances are present in the fermentation broth or the fermentation broth depleted of microorganisms from step (α), which could disrupt the subsequent steps of the method according to the invention, particularly the crystallization carried out in preferred embodiments and still to be described in detail.

In a preferred embodiment, step (I-0) is carried out continuously, i.e. the reactants are fed continuously to the fermentation reactor and the product is withdrawn continuously from the fermentation reactor. In continuous process regimes, the microorganism under some circumstances is discharged with the product stream; the microorganism however generally reproduces itself such that feeding of fresh microorganism is generally unnecessary (but if necessary can of course be done). Cell retention to avoid discharge of microorganism is also possible.

In another preferred embodiment, step (I-0) is carried out in a discontinuous process regime (so-called "batchwise mode"). In one variant of the discontinuous procedure (so-called "Fed batch mode"), the reactants are fed continuously to the fermentation reactor as long as the reactor volume allows it without products being removed from the reactor. The reaction is interrupted after addition of the maximum possible amount of reactants and the product mixture is withdrawn from the fermentation reactor.

Irrespective of the exact procedure, the fermentation reactor preferably comprises devices for measuring important process parameters such as temperature, pH of the fermentation broth, concentration of substrate and product, dissolved oxygen content, cell density of the fermentation broth. In particular, the fermentation reactor preferably comprises devices for adjusting at least one (preferably all) of the aforementioned process parameters.

Suitable fermentation reactors are stirred tanks, membrane reactors, plug flow reactors or loop reactors (see for example Bioprozesstechnik, Horst Chmiel, ISBN-10: 3827424763, Spektrum Akademischer Verlag). Particularly preferred for both aerobic and anaerobic fermentations are stirred tank reactors and loop reactors (particularly airlift reactors in which circulation of the liquid in the reactor is achieved by sparging).

It has been found to be useful not to directly decarboxylate the fermentation broth, optionally after work-up according to step (α) and/or step (β) (although this is possible in principle), but to enrich aminobenzoic acid beforehand in a suitable manner (step (I-0) (a)). This may be accomplished for example by
(1) evaporation of the fermentation broth or
(2) precipitation combined with at least partial removal of the aminobenzoic acid that separates out from the mother liquor.

Preference is given in accordance with the invention to variant (2). In the precipitation, the fermentation broth, optionally worked-up as outlined above according to step (α), and/or step (β), is subjected to an acid treatment. During this acid treatment, aminobenzoic acid separates out (up to a proportion corresponding to the solubility limit) (crystallizes out). In this variant (2), the acid treatment for the precipitation comprises the optionally required acid treatment outlined above for converting the aminobenzoic acid of step (I-0) to the electroneutral form. The aminobenzoic acid separated out can then be filtered off and further processed. It is also possible to separate off only a portion of the mother liquor obtained in the acid treatment (crystallization) and to recycle the remaining suspension of aminobenzoic acid in mother liquor to the decarboxylation in step (I).

In a particularly preferred configuration of the invention, step (I-0) (a) is carried out as follows:
(i) treatment, preferably single-stage treatment, of the fermentation broth obtained in step (I-0), optionally after carrying out step (α) and/or step (β), in a reactor with acid such that aminobenzoic acid separates out from the fermentation broth, wherein preferably the pH of the resulting mixture is adjusted to a value in the range from 3.0 to 4.7, preferably in the range from 3.2 to 3.7, particularly preferably in the range from 3.4 to 3.6;
(ii) at least partially removing the aminobenzoic acid that separates out in step (I-0) (a) (i) from the acid-treated fermentation broth (the mother liquor);
(iii) optional further purification of the aminobenzoic acid obtained in step (I-0) (a) (ii), preferably by washing with water.

In step (I-0) (a) (i) of the method according to the invention, the pH is adjusted by adding acid to the fermentation broth so that aminobenzoic acid crystallizes out. This type of crystallization is also referred to as reactive crystallization. This is preferably accomplished such that the pH of the resulting mixture corresponds to, or at least approximates to, that of the isoelectric point of the isomer of aminobenzoic acid to be separated off. Therefore, in the case of ortho-aminobenzoic acid as desired product, the pH is preferably adjusted to a value in the range of 3.0 to 4.7, particularly preferably to a value in the range of 3.2 to 3.7, especially preferably to a value in the range of 3.4 to 3.6, i.e. close to or corresponding to the isoelectric point at pH 3.5. This isoelectric point for the two other isomers of aminobenzoic acid is in each case at about pH 3.7. The acid treatment in step (I-0) (a) (i) is in this case preferably "single-stage" in the sense that the desired target pH is directly adjusted by adding acid without intermediate steps (such as filtration, centrifugation, column chromatography treatment and the like) being carried out at pH values between the starting pH (i.e. the pH of the fermentation broth obtained in step (I-0), optionally after carrying out step (α) and/or step (β)) and the target pH (i.e. the pH which is set after completion of the acid treatment in step (I-0) (a) (i)).

Suitable acids to be used in step (I-0) (a) (i) are all acids with which a pH can be set which corresponds or at least approximates to the isoelectric point of the desired aminobenzoic acid isomer. For this purpose, preference is given to strong mineral acids, particularly hydrochloric acid, sulfuric acid and/or phosphoric acid. The acid used in step (I-0) (a) (i) preferably comprises hydrochloric acid, particularly preferably hydrochloric acid at a concentration of 15% by mass to 37% by mass, especially preferably hydrochloric acid at a concentration of 18% by massto 25% by mass. It is particularly preferable that the acid, besides this hydrochloric acid with the exception of recycled mother liquor of step (I-0) (a) (ii) optionally added, does not comprise any further acid (i.e. no further acid is added from an external source). If a mixture of hydrochloric acid and a portion of the mother liquor obtained in step (I-0) (a) (ii) is used as acid used in step (I-0) (a) (i), preferably 1.0% by mass to 50% by mass of the total mother liquor obtained in step (I-0) (a) (ii) is mixed with hydrochloric acid.

Suitable as reactor in step (I-0) (a) (i) are customary configurations of chemical reactors familiar to those skilled in the art. Examples include stirred tanks or forced circulation crystallizers such as the "Oslo type". The addition of the fermentation broth obtained in step (I-0), optionally after carrying out step (α) and/or step (β), and the addition of acid to the reactor are preferably conducted continuously. The method product of step (I-0) (a) (i)—i.e. aminobenzoic acid suspended in acidified fermentation broth [=mother liquor]—is in this case withdrawn from the reactor at least in batches or preferably also continuously. In this case, also the further treatment in step (I-0) (a) (ii) is preferably carried out batchwise or continuously.

Step (I-0) (a) (ii), the at least partial removal of the aminobenzoic acid that separates out in step (I-0) (a) (i), is known per se from the prior art and is preferably carried out according to the invention by filtration or centrifugation. This step is preferably carried out as described in WO 2015/124687 A1. Reference is made here in particular to WO 2015/124687 A1, page 17, line 13 to page 17, line 16. Filtration can be carried out at reduced pressure, atmospheric pressure or elevated pressure. Centrifugation can be carried out using commercial centrifuges. It is also possible to let the suspension obtained in step (I-0) (a) (i) stand until the precipitated crystals of aminobenzoic acid settle out and then to decant off or aspirate off the supernatant mother liquor. The remaining crystals of aminobenzoic acid still wetted with mother liquor can be fed to step (I).

The optional step (I-0) (a) (iii), the further purification of the aminobenzoic acid obtained in step (I-0) (a) (ii), is known per se from the prior art (see especially WO 2015/124687 A1 and particularly WO 2015/124687 A1, page 18, line 4 to page 18, line 6) and is preferably carried out by one or more washes with aqueous washing media, especially water. In order to avoid yield losses, the pH of the aqueous wash medium can be adjusted to the same value as in step (I-0) (a) (i) after completion of the acid addition; therefore, in this embodiment, the washing is carried out with dilute acid instead of water, especially the same acid as used in step (I-0) (a) (i).

In a further preferred configuration of the invention, to the stream containing aniline fed back in step (III) to the reactor of step (I) is added solid or dissolved or suspended aminobenzoic acid, preferably specifically in such an amount that the mass stream of this supplied solid or dissolved or suspended aminobenzoic acid corresponds to the mass stream of the portion of the stream containing aniline withdrawn in step (I) fed to the purification in step (II). This embodiment is applicable to all variants of the invention, i.e. also to chemical production of the aminobenzoic acid to be decarboxylated. The production by fermentation of the aminobenzoic acid to be decarboxylated is however also preferred here. This procedure enables the feeding of the product of the fermentation step to the decarboxylation step in a simple manner. For this purpose, very particular preference is given to using aminobenzoic acid originating from step (I-0) (a), especially from step (I-0) (a) (ii) or from step (I-0) (a) (iii), as aminobenzoic acid. This aminobenzoic acid may be present as a suspension (for example if the aminobenzoic acid in step (I-0) (a) is enriched by substantial evaporation) or solution (for example if the aminobenzoic acid in step (I-0) (a) is enriched by minimal evaporation) or solid (for example if the aminobenzoic acid in step (I-0) (a) is enriched by acid treatment and subsequent isolation of the precipitated aminobenzoic acid).

In each case, said aminobenzoic acid from step (I-0) (a), especially from step (I-0) (a) (ii) or from step (I-0) (a) (iii) contains water. In the case of a solution or suspension this is necessarily the case (since it is in the nature of aqueous solutions or suspensions). In the case of a solid, it is ensured that this is not, or at least not completely, dried, but is still wetted with residues of mother liquor or preferably wash water.

In this embodiment, the water content and the amount of this aminobenzoic acid are preferably adjusted so that the water content of the liquid reaction mixture in step (I), determined by Karl Fischer titration, is in the range of 0.10% by mass to 40% by mass, preferably 0.15% by mass to 20% by mass, based on the total mass of the liquid reaction mixture of step (I). In this embodiment, therefore, the aminobenzoic acid to be decarboxylated in step (I) is dissolved in the recirculated stream containing aniline. This procedure is particularly cost-effective since an additional solvent extraneous to the system for the aminobenzoic acid to be decarboxylated can be omitted (which also simplifies the further work-up, since a separation of aniline and solvent extraneous to the system is not required) and a further feed unit can be dispensed with.

An as an alternative, it is of course also possible to feed the stream containing aniline recirculated in step (III) and the aminobenzoic acid to be decarboxylated to the reactor of step (I) via separate feed units (i.e. without pre-mixing).

The procedure according to the invention, in which the decarboxylation is carried out in a reaction medium which largely consists of portions of recirculated crude product (recirculated aniline comprising the crude unpurified aniline), has many advantages compared to the variant in which only purified aniline (and optionally solvent extraneous to the system such as 1-dodecanol) is used as solvent:

The aniline obtained in step (II), apart from comparatively low portions which are optionally mixed with the stream containing aniline to be recirculated to the reactor of step (I), is directly available for sale or further reaction to aniline conversion products.

The use of crude aniline is of particular economic advantage with regards to operating costs (particularly energy costs) and investment costs (particularly as far as plant size is concerned).

In a preferred configuration, no costs accrue for solvents extraneous to the system.

The procedure according to the invention furthermore enables the problem-free use of moist reactant (aminobenzoic acid) in comparison to the decarboxylation in 1-dodecanol known from the prior art, in particular, based on the total mass of reactant to be used, of up to 40% by mass of reactant containing water as starting material, which has a positive effect on the operating and investment costs of the crystallization step used in preferred configurations [step (I-0) (a) (i) to (ii) or (i) to (iii)], since a drying step can be omitted or can at least be more simply configured.

FIG. 1 shows a preferred configuration of the method according to the invention.

List of Reference Symbols:
Apparatus:
A) Fermentation reactor
B) Cell separation
C) Reactor for crystallization
D) Filter/decanter
E) Reactor for decarboxylation
F) Distillation column Material streams:
1) Fermentable carbon-containing compound
2) Nitrogen-containing compound
3) Oxygen or air source for the fermentation reactor in the case of aerobic fermentations
4) Fermentation broth with microorganisms
5) Microorganisms recirculated to the fermentation reactor
6) Fermentation broth depleted of microorganisms (especially freed of microorganisms)
7) Acid (particularly hydrochloric acid) for precipitating aminobenzoic acid
8) Suspension of aminobenzoic acid
9) Mother liquor for further work-up
10) Suspension of aminobenzoic acid crystals
11) Crude aniline recirculation
12) Crude aniline stream for distillation
13) Bottoms stream of the aniline distillation (predominantly high-boiling by-products)
14) Purified aniline for further use The aniline obtained according to the invention is preferably further reacted to give an aniline conversion product, i.e. step (IV) is preferably carried out. Selected further reactions of the aniline obtained in step (IV) are:

(IV-1) acid-catalyzed reaction of aniline with formaldehyde to form di- and polyamines of the diphenylmethane series;
(IV-2) acid-catalyzed reaction of aniline with formaldehyde, followed by reaction with phosgene to form di- and polyisocyanates of the diphenylmethane series;
(IV-3) reacting aniline to give an azo compound.

The further reaction of aniline with formaldehyde to give di- and polyamines of the diphenylmethane series (IV-1) is known per se and may be carried out by any method of the prior art. The continuous or partially discontinuous preparation of di- and polyamines of the diphenylmethane series from aniline and formaldehyde is disclosed e.g. in EP 1 616 890 A1, U.S. Pat. No. 5,286,760, EP-A-451442 and WO-A-99/40059. The reaction is effected under acid catalysis. Suitable as acidic catalyst is preferably hydrochloric acid.

The further reaction of the di- and polyamines of the diphenylmethane series thus obtained with phosgene to give di- and polyisocyanates of the diphenylmethane series (IV-2) is also known per se and may be carried out by any method of the prior art. Suitable methods are described, for example, in EP 2 077 150 B1, EP 1 616 857 A1, EP 1 873 142 A1, and EP 0 314 985 B1.

The conversion of the aniline obtained according to the invention to azo compounds, especially to azo dyes (IV-3) can be carried out by any method of the prior art. Reference may be made by way of example to the known production of aniline yellow (para-aminoazobenzene; CAS 493-5-7) or indigo (2,2'-bis(2,3-dihydro-3-oxomethylidene); CAS 482-89-3) (Per Wiklund et al., *Current Organic Synthesis*, 2006, 3, 379-402).

EXAMPLES

In all examples, the ortho-aminobenzoic acid (oAB) used in each case was produced by fermentation of recombinant *Corynebacterium glutamicum* ATTC-13032 strains which have a deletion or reduced expression of the trpD gene, which encodes anthranilate phosphoribosyl transferase, such as described in WO 2015/124687 A1, example 3 (corresponds to step (I-0) of the method according to the invention). To deplete the microorganism used, the fermentation broth was filtered (corresponds to step (I-0) (a) of the method according to the invention). The oAB was isolated from the fermentation broth by crystallization by adding hydrochloric acid, filtration and washing with water (corresponds to step (I-0) (a), variant (2) of the method according to the invention).

Example 1a (Comparative Example)

Ortho-aminobenzoic acid (oAB) is dissolved in aniline (Sigma Aldrich, >99% purity) such that a solution having a proportion by mass of oAB of 40% is obtained. A viscous suspension is obtained at room temperature which goes into solution on increasing the temperature to 60 to 80° C. 100 g of this solution are transferred to an autoclave as reactor, in which there are 8.00 g of zeolite catalyst H-Y (CBV-600 from Zeolyst International, pretreated for removal of moisture according to manufacturer's instructions). The reactor is sealed and purged with Ar in order to expel oxygen. The reaction mixture is heated to 180° C. This temperature is maintained for 1.0 h. The pressure increase (arising from $CO_2$ evolution) is measured. Samples are also withdrawn at 10-minute intervals and analyzed by HPLC. No further pressure increase could be detected after 40 minutes; oAB had been converted by more than 99%. The reaction gave aniline with a selectivity of >98%.

Example 1b (Comparative Example)

Example 1a was repeated in the presence of 10% by mass water. The results are similar to example 1a. oAB had also been converted by more than 99% after 40 minutes. The reaction gave aniline with a selectivity of >98%.

Example 2 (Inventive)

After cooling, the crude product (86 g) of the reaction from example 1a is withdrawn from the reactor via a pipe provided with a filter. 60 g of this product are mixed with 40 g of oAB (proportion by mass of oAB 40%) and reintroduced into the reactor. The same reaction conditions as in example 1a are maintained. The catalyst is not exchanged. 10 reaction cycles are carried out in total. The conversion of oAB in the first reaction cycle was 98.8% and stabilized in the following reaction cycles to values between 97.7% and 98.2%.

Example 2 shows that the catalyst furthermore reliably produces aniline with high activity and selectivity despite recycling crude aniline 10 times. This was completely surprising; it would have been expected that the impurities of the crude aniline stream deactivate the catalyst.

The invention claimed is:

1. A method for producing aniline or an aniline conversion product, comprising:
   (I) decarboxylating aminobenzoic acid to aniline in a reactor in the presence of a catalyst, wherein a stream containing aniline is withdrawn from the reactor;
   (II) purifying a portion of the stream containing aniline withdrawn in step (I) to obtain aniline;
   (III) recirculating another portion of the stream containing aniline withdrawn in step (I) into the reactor of step (I); and
   (IV) optionally further reacting the aniline purified in step (II) to give an aniline conversion product.

2. The method of claim 1, in which a further aniline stream of purified aniline is fed to the reactor of step (I) in addition to the stream containing aniline recirculated in step (III), wherein the aniline additionally fed in the further aniline stream accounts for at most 60% of the total aniline fed to the reactor of step (I).

3. The method of claim 2, in which the concentration of aniline is monitored in the stream comprising aniline which is withdrawn from the reactor of step (I), and when a shortfall in the concentration of aniline of a previously set value is detected, the proportion of the further aniline stream of purified aniline additionally fed to the reactor is increased to a value of at most 60% of the aniline fed in total to the reactor of step (I).

4. The method of claim 1, in which the stream containing aniline withdrawn from the reactor of step (I) is divided into two streams in a ratio by mass in the range from 9.0:1 to 1:9.0, of which one stream is fed to the recirculation of step (III) and the other stream is fed to the purification of step (II).

5. The method of claim 1, in which step (I) is conducted at a temperature in the range from 140° C. to 240° C. and at an absolute pressure in the range from 1.00 bar to 20.0 bar.

6. The method of claim 1, in which the reactor of step (I)
   is a slurry phase reactor, and the catalyst is used at a concentration in the range from 0.100% by mass to 50.0% by mass, based on the total mass of the liquid reaction mixture
   or
   is a stirred tank reactor,
   or
   is a tubular reactor having a catalyst bed.

7. The method of claim 1, in which the catalyst used in step (I) is a zeolite catalyst.

8. The method of claim 1, in which the aminobenzoic acid to be decarboxylated in step (I) is provided by the following step (I-0) carried out prior to step (I):
   (I-0) fermentation of a raw material, which comprises at least
      one fermentable carbon-containing compound and
      one nitrogen-containing compound,
      in a fermentation reactor using microorganisms to obtain a fermentation broth; which is then optionally followed by the following work-up steps:
      (α) removing the microorganism from the fermentation broth
      and/or
      (β) decolorizing the fermentation broth or, in the case of step (α) being carried out, the fermentation broth depleted of microorganisms obtained in step (α).

9. The method of claim 8, in which the following step is carried out after step (I-0) and prior to step (I):
   (I-0) (a) enrichment of the aminobenzoic acid by:
      (1) evaporation of the fermentation broth, or
      (2) precipitation by acid treatment combined with at least partial removal of the aminobenzoic acid that separates out from the acid-treated fermentation broth.

10. The method of claim 9, in which step (I-0) (a) is carried out according to variant (2) and comprises:
   (i) treating the fermentation broth obtained in step (I-0), optionally after carrying out step (α) and/or step (β), in a reactor with acid such that aminobenzoic acid separates out from the fermentation broth;
   (ii) at least partially removing the aminobenzoic acid that separates out in step (I-0) (a) (i) from the acid-treated fermentation broth; and
   (iii) optional further purification of the aminobenzoic acid obtained in step (I-0) (a) (ii).

11. The method of claim 10, in which the acid used in step (I-0) (a) (i) comprises hydrochloric acid, sulfuric acid and/or phosphoric acid.

12. The method of claim 8, in which the microorganisms used in step (I-0) comprise a species selected from the group consisting of *Escherichia coli, Pseudomonas putida, Corynebacterium glutamicum, Ashbya gossypii, Pichia pastoris, Hansenula polymorpha, Yarrowia lipolytica, Zygosaccharomyces bailii* and *Saccharomyces cerevisiae*.

13. The method of claim 1, wherein solid or dissolved or suspended aminobenzoic acid is added to the stream containing aniline recirculated in step (III) into the reactor of step (I).

14. The method of claim 9, wherein solid or dissolved or suspended aminobenzoic acid is added to the stream containing aniline recirculated in step (III) into the reactor of step (I).

15. The method of claim 14, wherein sold or dissolved or suspended aminobenzoic acid is added to the stream containing aniline recirculated in step (III) into the reactor of step (I), wherein the solid or dissolved or suspended aminobenzoic acid originates from step (I-0) (a) and contains water.

16. The method of claim 1, wherein the stream containing aniline recirculated in step (III) and the aminobenzoic acid to be decarboxylated are fed to the reactor of step (I) via separate feed units.

17. The method of claim 1, wherein step (IV) is carried out.

18. The method of claim 17, wherein step (IV) includes one of the following reactions:
   (IV-1) acid-catalyzed reaction of aniline with formaldehyde to form di- and polyamines of the diphenylmethane series;
   (IV-2) acid-catalyzed reaction of aniline with formaldehyde, followed by reaction with phosgene to form di- and polyisocyanates of the diphenylmethane series; or
   (IV-3) reacting aniline to give an azo compound.

* * * * *